United States Patent [19]

Boroschewski et al.

[11] 4,317,674
[45] * Mar. 2, 1982

[54] DIURETHANES, PROCESS FOR MAKING THE SAME AND SELECTIVE HERBICIDE COMPOSITION CONTAINING SAME

[75] Inventors: Gerhard Boroschewski; Friedrich Arndt, both of Berlin, Fed. Rep. of Germany

[73] Assignee: Schering AG, Berlin and Bergkamen, Fed. Rep. of Germany

[*] Notice: The portion of the term of this patent subsequent to May 13, 1997, has been disclaimed.

[21] Appl. No.: 42,062

[22] Filed: May 24, 1979

Related U.S. Application Data

[63] Continuation of Ser. No. 848,094, Mar. 11, 1977, abandoned.

[30] Foreign Application Priority Data

Nov. 3, 1976 [DE] Fed. Rep. of Germany ....... 2650796

[51] Int. Cl.³ ................. A01N 37/44; C07C 125/075
[52] U.S. Cl. ........................................ 71/111; 560/27; 560/29
[58] Field of Search ................. 71/111; 560/29, 27

[56] References Cited

U.S. PATENT DOCUMENTS

| | | | |
|---|---|---|---|
| 3,404,975 | 10/1968 | Wilson et al. | 560/29 |
| 3,546,343 | 12/1970 | Payne et al. | 560/29 |
| 3,551,477 | 12/1970 | Koenig et al. | 560/29 |
| 3,692,820 | 9/1972 | Boroschewski et al. | 560/29 |
| 3,901,936 | 8/1975 | Boroschewski | 560/27 |
| 3,904,396 | 9/1975 | Boroschewski et al. | 560/29 |
| 4,202,684 | 5/1980 | Arndt et al. | 560/29 |

FOREIGN PATENT DOCUMENTS 1567151 6/1969 Fed. Rep. of Germany .

*Primary Examiner*—G. T. Breitenstein
*Attorney, Agent, or Firm*—Michael J. Striker

[57] ABSTRACT

Diurethanes of the formula

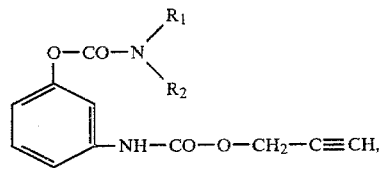

wherein $R_1$ is alkyl, alkenyl or halogenoalkyl and
$R_2$ is phenyl or phenyl substituted in one or more places by the same or different substituents selected from the group consisting of halogen, trifluoromethyl, alkyl and alkoxy.

25 Claims, No Drawings

DIURETHANES, PROCESS FOR MAKING THE SAME AND SELECTIVE HERBICIDE COMPOSITION CONTAINING SAME

This is a continuation of application Ser. No. 848,094, filed Mar. 11, 1977.

BACKGROUND OF THE INVENTION

The invention relates to diurethanes, processes for making the same, and a selective herbicidal composition containing same for preferred use in regard to soybeans.

The selective herbicidal action of diurethanes is known (see West Germany Pat. No. 1,567,151). A satisfactory herbicidal activity against weeds which are difficult to suppress, such as, Amaranthus sp., and an adequate selectivity in respect to soybeans could however so far not be established for the prior art products.

It is therefore an object of the invention to provide for a herbicide which combines general activity against weeds in post-emergence application with activity against special problem weeds and complete compatability with soybeans.

SUMMARY OF THE INVENTION

This object is met by a composition which contains at least one compound of the formula

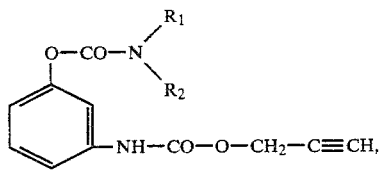

in which $R_1$ is alkyl, alkenyl or halogenoalkyl and $R_2$ is phenyl or phenyl substituted in one or more places by the same or different substituents selected from the group consisting of halogen, trifluoromethyl, alkyl and alkoxy.

The diurethanes of the invention are particularly distinguished by their surprisingly high compatibility for soybeans.

The highest activity is observed with these compounds if they are applied in post-emergence application.

The compounds of the invention also have a broad spectrum of activity. Their herbicidal action comprises many different plant species as, for instance, Stellaria, Senecio, Lamium, Centaurea, Amarantus, Chrysanthemum, Ipomea, Polygonum, and Galium. Their compatibility is good apart from soybeans, also for potatoes, grains, maize, rice and sorghum.

The compounds are usually applied in amounts of about 0.5 to 5 kg of active agent per about 2.5 acres.

DETAILS OF THE INVENTION AND PREFERRED EMBODIMENTS

The diurethanes of the invention can be used either by themselves or intermixed with each other or in mixture with other active agents. Depending on the particular purpose the other herbicidal agents which may be used in connection with the compounds of the invention are among others following. It is noted that these additives may be added only immediately prior to use:

substituted anilines,
substituted aryloxycarboxylic acids and their salts, esters and amides,
substituted ethers,
substituted arsonic acids and their salts, esters and amides,
substituted benzimidazoles,
substituted benzisothiazoles,
substituted benzthiadiazinone dioxides,
substituted benzoxazines,
substituted benzthiazoles,
substituted benzthiadiazines
substituted biurets,
substituted quinolines,
substituted carbamates,
substituted aliphatic carboxylic acids and their salts, esters and amides,
substituted aromatic carboxylic acids and their salts, esters and amides,
substituted carbamoylalkyl-thio- or dithiophosphates
substituted quinazolines,
substituted cycloalkylamidocarbonylthiol acids and their salts, esters and amides,
substituted cycloalkylcarbonylamido-thiazoles,
substituted dicarboxylic acids and their salts, esters and amides,
substituted dihydrobenzofuranylsulfonates,
substituted disulfides,
substituted dipyridyl salts,
substituted dithiocarbamates,
substituted dithiophosphoric acids and their salts, esters and amides,
substituted urea derivatives,
substituted hexahydro-1H-carbothioates,
substituted hydantoines,
substituted hydrazides,
substituted hydrazonium salts,
substituted isoxazolpyrimidones,
substituted imidazoles,
substituted isothiazolpyrimidones,
substituted ketones,
substituted naphthoquinones,
substituted aliphatic nitriles,
substituted aromatic nitriles,
substituted oxadiazoles,
substituted oxadiazinones,
substituted oxadiazolidinediones,
substituted oxadiazinediones,
substituted phenols and their salts, esters and amides,
substituted phosphonic acids and their salts, esters and amides,
substituted phosphoniumchlorides,
substituted phosphonalkylglycines,
substituted phosphites,
substituted phosphoric acids and their salts, esters and amides,
substituted piperidines,
substituted pyrazoles,
substituted pyrazolalkylcarboxylic acids and their salts, esters, and amides,
substituted pyrazolium salts,
substituted pyrazoliumalkylsulfates,
substituted pyridazines,
substituted pyridazones,
substituted pyridine-carboxylic acids and their salts, esters and amides,
substituted pyridines,
substituted pyridinecarboxylates,
substituted pyridinones, substituted pyrimidones,
substituted pyrrolidine-carboxylic acids and their salts, esters and amides,
substituted pyrrolidines,
substituted arylsulfonic acids and their salts, esters and amides,
substituted styrenes,
substituted tetrahydro-oxadiazindiones,
substituted tetrahydromethanoindenes,
substituted tetrahydro-diazol-thiones,
substituted tetrahydro-thiadiazine-thiones,
substituted tetrahydro-thiadiazinediones,
substituted thiadiazoles,
substituted aromatic thiocarboxylic acid amides,
substituted thiocarboxylic acids and their salts, esters and amides,
substituted thiolcarbamates,
substituted thiophosphoric acids and their salts, esters and amides,
substituted triazines,
substituted triazoles
substituted uracils, and
substituted urethidindiones.

It is also possible to use other additives, for instance, non-phytotoxic additives which result in a synergistic increase of action in herbicides such as wetting agents, emulsifiers, solvents and oily additives.

The compounds of the inventions or their mixtures are preferably used in the form of compositions such as powders, dusting agents, granulates, solvents, emulsions or suspensions. There are then added liquid and/or solid carrier materials or diluents and, if desired, wetting agents, adhesion promoting agents, emulsifiers and/or dispersing agents.

Suitable liquid carrier materials are, for instance, water, aliphatic and aromatic hydrocarbons such as benzene, toluene, xylene, cyclohexanone, isophorone, dimethylsulfoxide, dimethylformamide, and furthermore mineral oil fractions.

As solid carrier materials there may be used mineral earths as, for instance, tonsil, silicagel, talcum, kaolin, attaclay, limestone, silicic acid and plant products, for instance flours.

There may also be added surface active agents such as, for instance, calciumlignosulfonate, polyoxyethylenealkylphenyl-ethers, naphthalinesulfonic acid and their salts, phenolsulfonic acid and their salts, formaldehyde condensation products, fatty alcohol sulfates, as well as substituted benzolsulfonic acids and their salts.

The proportion of active agents in the different compositions can be varied widely. The compositions may, for instance, contain about 10 to 80% by weight of active agents, 90 to 20% by weight of liquid or solid carrier materials and, if desired, up to 20% by weight of surface active agents.

The application of the compositions can be practiced in conventional form, for instance, with water as carrier material in spray amounts of about 100 to 1000 liters per about 2.5 acres. The application of the compositions is possible in the so-called "low-volume" or "ultra-low-volume" process and in the form of so-called microgranulates.

Among the diurethanes of the invention those are particularly characterized by a selective action with regard to soybeans in which in the above-given general formula $R_1$ is $C_1$-$C_4$-alkyl, $C_2$-$C_4$-alkenyl, halogeno-$C_1$-$C_4$-alkyl and $R_2$ is phenyl, $C_1$-$C_3$-alkylphenyl, $C_1$-$C_3$-alkoxyphenyl, chlorophenyl, dichlorophenyl, trifluoromethylphenyl.

Most preferred among these compounds are those in which in the above general formula $R_1$ is methyl, ethyl, propyl, isopropyl, butyl, isobutyl, chloroethyl, bromoethyl or allyl and $R_2$ is phenyl, methylphenyl, dimethylphenyl, chlorophenyl, dichlorophenyl, chloromethylphenyl, methoxyphenyl, trifluoromethylphenyl, ethylphenyl, fluorophenyl, methoxy-methylphenyl, fluoromethylphenyl or cyclohexyl.

PROCESS OF MAKING

The compounds of the invention which have not been described so far in the literature can be made by various processes as follows:

I. The chloroformic acid ester of 3-hydroxycarbanilic acid propargylester of the formula

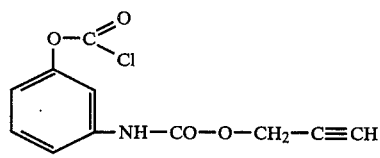

is reacted with an amine of the formula

in the presence of an acid acceptor, for instance, an excess of amine or an inorganic base such as sodium hydroxide, sodium carbonate or potassium carbonate, or a tertiary organic base such as triethylamine.

II. The 3-hydroxycarbanilic acid propargylester of the formula

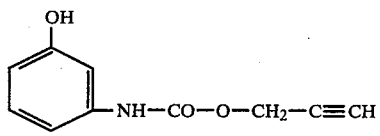

is reacted with carbamoylchloride of the formula

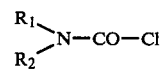

in the presence of a tertiary organic base as for instance triethylamine or pyridine, or in the form of an alkali salt.

In both of the above cases $R_1$ and $R_2$ have the same meaning as given in the above general compound formula. In both cases the reaction is carried out at temperatures of 0° to 100° C. and after completion of the reaction the reaction products are isolated in conventional manner.

The starting products for the processes of the invention are known or can be produced by obvious known processes.

EXAMPLES

The following examples will further illustrate the invention.

EXAMPLE 1

N-isobutyl-4-methylcarbanilic acid-[3-(2-propinyloxycarbonylamino)-phenyl]-ester A solution of 25.4 g (0.1 mol) of chloroformic acid-3-(2-propinyl-oxycarbonylamino)-phenylester in 100 ml acetic acid ethylester is added within a period of 20 minutes to a solution of 16.3 g (0.1 mol) of N-isobutyl-p-toluidine in 50 ml acetic acid ethylester. Simultaneously a solution of 13.8 g (0.1 mol) of potassium carbonate in 50 ml water is added dropwise while stirring and cooling to 15° C. temperature. Thereafter, the solution is further stirred at 15° C. for 30 minutes. The organic phase is then separated and washed at 0° C. with dilute sodium hydroxide, dilute hydrochloric acid and water. After drying on magnesium sulfate the mass is concentrated at a reduced pressure. It is then recrystallized from acetic acid ethylester/pentane.

Yield: 27 g = 71% of the theoretical. m.p.: 106°–107° C.

Analysis: calculated: C: 69.45%; H: 6.36%; N: 7.36%; obtained: C: 69.42%; H: 6.37%; N: 7.22%.

The following diurethanes were made in an analogous manner.

| Compound | Physical Constant |
|---|---|
| N-propylcarbanilic acid-[3-(2-propinyl-oxycarbonylamino)-phenyl]-ester | m.p.: 118–120° C. |
| N-(1-methylethyl)-carbanilic acid-[3-(2-propinyloxycarbonylamino)-phenyl]-ester | m.p.: 157–159° C. |
| N-butylcarbanilic acid-[3-(2-propinyl-oxycarbonylamino)-phenyl]-ester | $n_D^{20}$ = 1,5475 |
| N-ethylcarbanilic acid-[3-(2-propinyloxycarbonylamino)-phenyl]-ester | m.p.: 168–170° C. |
| N-ethyl-3-chlorocarbanilic acid-[3-(2-propinyloxycarbonylamino)-phenyl-ester | m.p.: 146–148° C. |
| N-allylcarbanilic acid-[3-(2-propinyloxycarbonylamino)-phenyl]-ester | m.p.: 118–120° C. |
| N-ethyl-3-methylcarbanilic acid-[3-(2-(2-propinyloxycarbonylamino)-phenyl]-ester | m.p.: 154–156° C. |
| N-ethyl-4-methylcarbanilic acid-[3-(2-propinyloxycarbonylamino)-phenyl]-ester | m.p.: 101–103° C. |
| N-(2-bromoethyl)-carbanilic acid-[3-(2-propinyloxycarbonylamino)-phenyl]-ester | m.p.: 105–106° C. |
| N-(2-chloroethyl)-carbanilic acid-[3-(2-propinyloxycarbonylamino)-phenyl]-ester | m.p.: 121–123° C. |
| 3-chloro-N-methylcarbanilic acid-[3-(2-propinyloxycarbonylamino)-phenyl]-ester | m.p.: 130–132° C. |
| N-ethyl-2-methylcarbanilic acid-[3-(2-propinyloxycarbonylamino)-phenyl]-ester | m.p.: 161–162° C. |
| N-Methylcarbanilic acid-[3-(2-propinyl-oxycarbonylamino)-phenyl]-ester | m.p.: 146–147° C. |
| N-(2-methylpropyl)-carbanilic acid-[3-(2-propinyloxycarbonylamino)-phenyl]-ester | m.p.: 97–99° C. |
| 4,N-dimethylcarbanilic acid-[3-(2-propinyloxycarbonylamino)-phenyl]-ester | m.p.: 146–149° C. |
| 3,N-dimethylcarbanilic acid-[3-(2-propinyloxycarbonylamino)-phenyl]-ester | m.p.: 142–144° C. |
| 2,N-dimethylcarbanilic acid-[3-(2-propinyloxycarbonylamino)-phenyl]-ester | m.p.: 149–150° C. |
| N-ethyl-3,4-dichlorocarbanilic acid-[3-(2-propinyloxycarbonylamino)-phenyl]-ester | m.p.: 104–105° C. |
| N-allyl-2-methylcarbanilic acid-[3-(2-propinyloxycarbonylamino)-phenyl]-ester | m.p.: 104–105° C. |
| N-isobutyl-4-methylcarbanilic acid-[3-(2-propinyloxycarbonylamino)-phenyl]-ester | m.p.: 106–107° C. |
| 4-chloro-N-methylcarbanilic acid-[3-(2-propinyloxycarbonylamino)-phenyl]-ester | m.p.: 128–128.5° C. |
| 3,4-dichloro-N-methylcarbanilic acid[3-(2-propinyloxycarbonylamino)-phenyl]-ester | m.p.: 98–99° C. |
| 3-methyl-N-propylcarbanilic acid-[3-(2-propinyloxycarbonylamino)-phenyl]-ester | m.p.: 93–95° C. |
| 2-methyl-N-propylcarbanilic acid-[3-(2-propinyloxycarbonylamino)-phenyl]-ester | m.p.: 97–99° C. |
| N-isobutyl-3-methylcarbanilic acid-[3-(2-propinyloxycarbonylamino)-phenyl]-ester | m.p.: 111–113° C. |
| 3,5-dichloro-N-methylcarbanilic acid-[3-(2-propinyloxycarbonylamino)-phenyl]-ester | m.p.: 156–158° C. |
| N-butyl-2-methyl-carbanilic acid-[3-(2-propinyloxycarbonylamino)-phenyl]-ester | m.p.: 89–91° C. |
| N-ethyl-4-chloro-carbanilic acid-[3-(2-propinyloxycarbonylamino)-phenyl]-ester | m.p.: 104–106° C. |
| N-ethyl-3,5-dichlorocarbanilic acid-[3-(2-propinyloxycarbonylamino)-phenyl]-ester | m.p.: 154–155° C. |
| N-(2-bromoethyl)-3-chlorocarbanilic acid-[3-(2-propinyloxycarbonylamino)-phenyl]-ester | m.p.: 115–117° C. |
| N-Methyl-3-trifluoromethylcarbanilic acid-[3-(2-propinyloxycarbonylamino)-phenyl]-ester | m.p.: 80–82° C. |
| N-butyl-3-methylcarbanilic acid-[3-(2-propinyloxycarbonylamino)-phenyl]-ester | $n_D^{20}$ = 1,5525 |
| 2-chloro-N-methylcarbanilic acid-(3-2-propinyloxycarbonylamino)-phenyl]-ester | m.p.: 147–148° C. |
| N-ethyl-2-chlorocarbanilic acid-[3-(2-propinyloxycarbonylamino)-phenyl]-ester | m.p.: 143–144° C. |
| N-(2-bromoethyl)-3-trifluoromethylcarbanilic acid-[3-(2-propinyloxycarbonylamino)-phenyl]-ester | m.p.: 86–88° C. |
| N-(2-bromoethyl)-4-chlorocarbanilic acid-[3-(2-propinyloxycarbonylamino)-phenyl]-ester | $n_D^{20}$ = 1,5830 |
| N-ethyl-3-trifluoromethylcarbanilic acid-[3-(2-propinyloxycarbonylamino)-phenyl]-ester | m.p.: 111–113° C. |

The compounds of the invention are soluble in acetone, cyclohexanone, acetic acid ethylester, isophorone, tetrahydrofuran, dioxane, dimethylformamide, dimethylsulfoxide, hexamethylphosphoric acid triamide. They are virtually unsoluble in water and light gasoline.

The following examples will further exemplify the activity of the compounds.

EXAMPLE 2

The compounds listed in the following Table 1 were applied in a hothouse in amounts of 5 kg of active agent per about 2.5 acres dissolved in 600 liter water per about 2.5 acres to Sinapis and Solanum as test plants by spraying in a post-emergence application. The results were evaluated three weeks after application on a scale from 0 = no effect to 4 = total destruction of the plants.

As appears from the table normally a destruction of the test plants was accomplished.

TABLE I

| Compound | post-emergence application | |
|---|---|---|
| | Sinapis | Solanum |
| N-propylcarbanilic acid-[3-(2-propinyloxycarbonylamino)-phenyl]-ester | 4 | 4 |
| N-(1-methylethyl)-carbanilic acid-[3-(2-propinyloxycarbonyl-amino)-phenyl]-ester | 4 | — |
| N-butylcarbanilic acid-[3-(2-propinyloxycarbonylamino)-phenyl]-ester | 4 | 4 |
| N-ethylcarbanilic acid-[3-(2-propinyloxycarbonylamino)-phenyl]-ester | — | — |
| N-ethyl-3-chlorocarbanilic acid- | | |

TABLE I-continued

| Compound | post-emergence application | |
|---|---|---|
| | Sinapis | Solanum |
| [3-(2-propinyloxycarbonylamino)-phenyl]-ester | 4 | 4 |
| N-allylcarbanilic acid-[3-(2-propinyloxycarbonylamino)-phenyl]-ester | 4 | 4 |
| N-ethyl-3-methylcarbanilic acid-[3-(2-propinyloxycarbonylamino)-phenyl]-ester | — | — |
| N-ethyl-4-methylcarbanilic acid-[3-(2-propinyloxycarbonylamino)-phenyl]-ester | 4 | — |
| N-(2-bromoethyl)-carbanilic acid-[3-(2-propinyloxycarbonylamino)-phenyl]-ester | 4 | 4 |
| N-(2-chloroethyl)-carbanilic acid-[3-(2-propinyloxycarbonylamino)-phenyl]-ester | 4 | 4 |
| 3-chloro-N-methylcarbanilic acid-[3-(2-propinyloxycarbonylamino)-phenyl]-ester | 4 | 4 |
| N-ethyl-2-methylcarbanilic acid-[3-(2-propinyloxycarbonylamino)-phenyl]-ester | — | — |
| N-methylcarbanilic acid-[3-(2-propinyloxycarbonylamino)-phenyl]-ester | 4 | 4 |
| N-(2-methylpropyl)-carbanilic-acid-[3-(2-propinyloxycarbonylamino)-phenyl]-ester | 4 | 4 |
| 4,N-dimethylcarbanilic acid-[3-(2-propinyloxycarbonylamino)-phenyl]-ester | 4 | — |
| 3,N-dimethylcarbanilic acid-[3-(2-propinyloxycarbonylamino)-phenyl]-ester | 4 | 4 |
| 2,N-dimethylcarbanilic acid-[3-(2-propinyloxycarbonylamino)-phenyl]-ester | — | — |
| N-ethyl-3,4-dichlorocarbanilic acid-[3-(2-propinyloxycarbonylamino)-phenyl]-ester | 4 | 4 |
| N-allyl-2-methylcarbanilic acid-[3-(2-propinyloxycarbonylamino)-phenyl]-ester | 4 | 4 |
| N-isobutyl-4-methylcarbanilic acid-[3-(2-propinyloxycarbonylamino)-phenyl]-ester | 4 | — |
| 4-chloro-N-methylcarbanilic acid-[3-(2-propinyloxycarbonylamino)-phenyl]-ester | 4 | 3 |
| 3,4-dichloro-N-methylcarbanilic acid-[3-(2-propinyloxycarbonylamino)-phenyl]-ester | 4 | 3 |
| 3-methyl-N-propylcarbanilic acid-[3-(2-propinyloxycarbonylamino)-phenyl]-ester | 4 | 4 |
| 2-methyl-N-propylcarbanilic acid-[3-(2-propinyloxycarbonylamino)-phenyl]-ester | 4 | — |
| N-isobutyl-3-methylcarbanilic acid-[3-(2-propinyloxycarbonylamino)-phenyl]-ester | 4 | — |
| 3,5-dichloro-N-methylcarbanilic acid-[3-(2-propinyloxycarbonylamino-phenyl]-ester | 4 | — |
| N-ethyl-4-chloro-carbanilic acid-[3-(2-propinyloxycarbonylamino)-phenyl]-ester | 4 | 4 |
| N-ethyl-3,5-dichlorocarbanilic acid-[3-(2-propinyloxycarbonylamino)-phenyl]-ester | 4 | — |
| N-(2-bromoethyl)-3-chlorocarbanilic acid-[3-(2-propinyloxycarbonylamino)-phenyl]-ester | 4 | 4 |
| N-methyl-3-trifluoromethylcarbanilic acid-[3-(2-propinyloxycarbonylamino)-phenyl]-ester | 4 | 4 |
| N-butyl-3-methylcarbanilic acid-[3-(2-propinyloxycarbonylamino)-phenyl]-ester | 4 | — |
| N-(2-bromoethyl)-4-chlorocarbanilic acid-[3-(2-propinyloxycarbonylamino-phenyl]-ester | 4 | 4 |
| N-ethyl-3-trifluoromethylcarbanilic acid-[3-(2-propinyloxycarbonylamino)-phenyl]-ester | 4 | 4 |
| N-butyl-2-methylcarbanilic acid-[3-(2-propinyloxycarbonylamino)-phenyl]-ester | 4 | — |

EXAMPLE 3

The plants listed below in Table 2 were treated in a hothouse in a similar test as in Example 1 in a post-emergence application with an amount of 3 kg of active agent per about 2.5 acres.

The comparison compound was 3-(methoxycarbonylaminophenyl)-N-(3-methylphenyl)-carbamate (Patent of the German Federal Republic No. 1,567,151).

The plants were in the growing stage. The applied amount of liquid was 500 liter per about 2.5 acres. The compounds were used in the form of emulsions. The results of the treatments were evaluated after 14 days on a scale from 0=total destruction to 10=no damage to the plants.

As appears from the Table 2 the compounds of the invention showed a high compatibility for soybeans and at the same time a good activity against weeds, while the comparison compound at a lower weed activity resulted in destruction of the agricultural plants.

TABLE II post-emergence application

| Compound | kg active agent per about 2.5 acres | soybean | Stellaria m. | Senecio v. | Matricaria ch. | Lamium a. | Centaurea c. | Amaranthus r. | Chrysanthemum s. | Ipomoea p. | Polygonum l. | Avena f. | Echinochloa c.g. | Setaria i. | Digitaria s. |
|---|---|---|---|---|---|---|---|---|---|---|---|---|---|---|---|
| N-propylcarbanilic acid-[3-(2-propinyloxycarbonylamino)-phenyl]-ester | 3 | 10 | 0 | 4 | 1 | 0 | 1 | 0 | 1 | 1 | 0 | 1 | 2 | 0 | 1 |
| N-butylcarbanilic acid-[3-(2-propinyloxycarbonylamino)-phenyl]-ester | 3 | 10 | 0 | 0 | 0 | 0 | 0 | 0 | 0 | 0 | 0 | 1 | 0 | 0 | 0 |
| N-ethyl-3-chlorocarbanilic acid-[3-(2-propinyloxycarbonylamino)-phenyl]-ester | 3 | 10 | 1 | 3 | 1 | 0 | 0 | 0 | 1 | 0 | 0 | 5 | 1 | 1 | 0 |
| N-allylcarbanilic acid-[3-(2-propinyloxycarbonylamino)-phenyl]-ester | 3 | 10 | 0 | 4 | 2 | 0 | 0 | 0 | 0 | 0 | 0 | 1 | 0 | 0 | 0 |
| N-ethyl-4-methylcarbanilic acid-[3-(2-propinyloxycarbonylamino)-phenyl]-ester | 3 | 10 | 0 | 4 | 1 | 0 | 0 | 0 | 0 | 2 | 0 | 2 | 1 | 1 | 0 |
| N-(2-bromoethyl)-carbanilic acid-[3-(2-propinyloxycarbonylamino)-phenyl]-ester | 3 | 10 | 0 | 0 | 0 | 0 | 0 | 0 | 0 | 0 | 0 | 2 | 4 | 0 | 0 |
| N-(2-chloroethyl)-carbanilic acid-(3-(2-propinyloxycarbonylamino)-phenyl]-ester | 3 | 10 | 0 | 2 | 0 | 0 | 0 | 0 | 0 | 0 | 0 | 2 | 4 | 0 | 0 |
| 3-chloro-N-methylcarbanilic acid-[3-(2-propinyloxycarbonylamino)-phenyl]-ester | 3 | 10 | 0 | 4 | 0 | 0 | 0 | 0 | 0 | 0 | 0 | 1 | 3 | 0 | 0 |
| N-Methylcarbanilic acid-[3-(2-propinyloxycarbonylamino)-phenyl]-ester | 3 | 10 | 0 | 4 | 2 | 0 | 0 | 0 | 2 | 0 | 0 | 3 | 0 | 0 | 0 |
| N-(2-methylpropyl)-carbanilic acid-[3-(2-propinyloxycarbonylamino)-phenyl]-ester | 3 | 10 | 0 | 1 | 0 | 0 | 0 | 0 | 0 | 0 | 1 | 2 | — | 1 | 3 |
| N-ethyl-3,4-dichlorocarbanilic acid-[3-(2-propinyloxycarbonylamino)-phenyl]-ester | 3 | 10 | 0 | 0 | 0 | 0 | 0 | 0 | 0 | 0 | 0 | 0 | 2 | 0 | 1 |
| 4-chloro-N-methylcarbanilic acid-[3-(2-propinyloxycarbonylamino)-phenyl]-ester | 3 | 10 | 0 | 0 | 0 | 0 | 1 | 0 | 0 | 2 | 0 | 5 | 2 | 0 | 4 |
| 3,4-dichloro-N-methylcarbanilic acid-[3-(2-propinyloxycarbonylamino)-phenyl]-ester | 3 | 10 | 0 | 0 | 0 | 0 | 0 | 0 | 0 | 0 | 0 | 5 | 2 | 3 | 3 |
| 3-methyl-N-propylcarbanilic acid-[3-(2-propinyloxycarboxyl-amino)-phenyl]-ester | 3 | 10 | 0 | 0 | 0 | 0 | 0 | 1 | 0 | 2 | 0 | 5 | 4 | 3 | 2 |
| N-isobutyl-3-methylcarbanilic acid-[3-(2-propinyloxycarbonylamino)-phenyl]-ester | 3 | 10 | 0 | 0 | 0 | 0 | 0 | 0 | 0 | 0 | 0 | 3 | 3 | 2 | 2 |

TABLE II-continued post-emergence application

| Compound | kg active agent per about 2.5 acres | soybean | Stellaria m. | Senecio v. | Matricaria ch. | Lamium a. | Centaurea c. | Amaranthus r. | Chrysanthemum s. | Ipomoea p. | Polygonum l. | Avena f. | Echinochloa c.g. | Setaria i. | Digitaria s. |
|---|---|---|---|---|---|---|---|---|---|---|---|---|---|---|---|
| N-butyl-2-methylcarbanilic acid-[3-(2-propinyloxycarbonylamino)-phenyl]-ester | 3 | 10 | 0 | 0 | 0 | 0 | 0 | 0 | 0 | 0 | 0 | 3 | 3 | 2 | 2 |
| N-ethyl-4-chlorocarbanilic acid-[3-(2-propinyloxycarbonylamino)-phenyl]-ester | 3 | 10 | 0 | 0 | 0 | 0 | 0 | 0 | 0 | 1 | 0 | 1 | — | 0 | 3 |
| N-ethyl-3,5-dichlorocarbanilic acid-[3-(2-propinyloxycarbonyl-amino)-phenyl]-ester | 3 | 10 | 1 | 2 | 0 | 0 | 1 | 1 | 0 | 0 | 0 | 1 | 3 | 0 | 4 |
| N-(2-bromoethyl)-3-chlorocarbanilic acid-[3-(2-propinyloxy)-phenyl]-ester | 3 | 10 | 1 | 1 | 0 | 0 | 0 | 1 | 1 | 0 | 0 | 2 | 4 | 3 | 1 |
| N-methyl-3-trifluoromethylcarbanilic acid-[3-(2-propinyloxycar-bonylamino)-phenyl]-ester | 3 | 10 | 0 | 0 | 0 | 0 | 0 | 0 | 0 | 0 | 0 | 0 | 4 | 0 | 1 |
| COMPARISON COMPOUND | | | | | | | | | | | | | | | |
| 3-(methoxycarbonylaminophenyl)-N-(3-methylphenyl)-carbamate | 2 | 2 | 2 | 2 | 0 | 1 | 0 | 8 | 0 | 3 | 10 | 10 | 8 | 0 | 8 |
| Untreated | | 10 | 10 | 10 | 10 | 10 | 10 | 10 | 10 | 10 | 10 | 10 | 10 | 10 | 10 |

What is claimed as new and desired to be protected by Letters Patent is set forth in the appended claims:

1. A selectively herbicidal compound particularly with soybeans of the formula

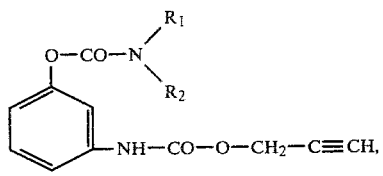

wherein $R_1$ is $C_1$–$C_4$ alkyl, $C_1$–$C_4$ alkenyl, chloro- $C_1$–$C_4$ alkyl or bromo- $C_1$–$C_4$ alkyl; and $R_2$ is phenyl or phenyl substituted in one or several places by one or more substituents selected from the group consisting of $C_1$–$C_3$ alkyl, $C_1$–$C_3$ alkoxy, trifluoromethyl, fluoro and chloro.

2. The compound of claim 1 which is 4,N-dimethylcarbanilic acid-[3-(2-propinyloxycarbonylamino)-phenyl]-ester.

3. The compound of claim 1 which is 3,N-dimethylcarbanilic acid-[3-(2-propinyloxycarbonylamino)-phenyl]-ester.

4. The compound of claim 1 which is 2,N-dimethylcarbanilic acid-[3-(2-propinyloxycarbonylamino)-phenyl]-ester.

5. The compound of claim 1 which is N-ethyl-3,4-dichlorocarbanilic acid-[3-(2-propinyloxycarbonylamino)-phenyl]-ester.

6. The compound of claim 1 which is N-allyl-2-methylcarbanilic acid-[3-(2-propinyloxycarbonylamino)-phenyl]-ester.

7. The compound of claim 1 which is N-isobutyl-4-methylcarbanilic acid-[3-(2-propinyloxycarbonylamino)-phenyl]-ester.

8. The compound of claim 1 which is 4-chloro-N-methylcarbanilic acid-[3-(2-propinyloxycarbonylamino)-phenyl]-ester.

9. The compound of claim 1 which is 3,4-dichloro-N-methylcarbanilic acid-[3-(2-propinyloxycarbonylamino)-phenyl]-ester.

10. The compound of claim 1 which is 3-methyl-N-propylcarbanilic acid-[3-(2-propinyloxycarbonylamino)-phenyl]-ester.

11. The compound of claim 1 which is 2-methyl-N-propylcarbanilic acid-[3-(2-propinyloxycarbonylamino)-phenyl]-ester.

12. The compound of claim 1 which is N-isobutyl-3-methylcarbanilic acid-[3-(2-propinyloxycarbonylamino)-phenyl]-ester.

13. The compound of claim 1 which is 3,5-dichloro-N-methylcarbanilic acid-[3-(2-propinyloxycarbonylamino)-phenyl]-ester.

14. The compound of claim 1 which is N-butyl-2-methyl-carbanilic acid-[3-(2-propinyloxycarbonylamino)-phenyl]-ester.

15. The compound of claim 1 which is N-ethyl-4-chloro-carbanilic acid-[3-(2-propinyloxycarbonylamino)-phenyl]-ester.

16. The compound of claim 1 which is N-ethyl-3,4-dichlorocarbanilic acid-[3-(2-propinyloxycarbonylamino)-phenyl]-ester.

17. The compound of claim 1 which is N-methyl-3-trifluoromethylcarbanilic acid-[3-(2-propinyloxycarbonylamino)-phenyl]-ester.

18. The compound of claim 1 which is N-butyl-3-methylcarbanilic acid-[3-(2-propinyloxycarbonylamino)-phenyl]-ester.

19. The compound of claim 1 which is 2-chloro-N-methylcarbanilic acid-[3-(2-propinyloxycarbonylamino)-phenyl]-ester.

20. The compound of claim 1 which is N-ethyl-2-chlorocarbanilic acid-[3-(2-propinyloxycarbonylamino)-phenyl]-ester.

21. The compound of claim 1 which is N-(2-bromoethyl)-3-trifluoromethylcarbanilic acid-[3-(2-propinyloxycarbonylamino)-phenyl]-ester.

22. The compound of claim 1 which is N-(2-bromoethyl)-4-chlorocarbanilic acid-[3-(2-propinyloxycarbonylamino)-phenyl]-ester.

23. The compound of claim 1 which is N-ethyl-3-trifluoromethylcarbanilic acid-[3-(2-propinyloxycarbonylamino)-phenyl]-ester.

24. A herbicidal composition comprising at least one active agent as defined in claim 1 in an amount between 10 and 80% by weight and about 90 to 20% by weight of liquid or solid carrier materials.

25. The composition of claim 24 which includes up to 20% by weight of surface active agents upon corresponding reduction of the liquid or solid carrier materials.